(12) United States Patent
Schiappa et al.

(10) Patent No.: US 11,975,152 B2
(45) Date of Patent: May 7, 2024

(54) ORAL CAPNOGRAPHY ACCESSORY DEVICE

(71) Applicant: OCA Holdings LLC, Lincolnwood, IL (US)

(72) Inventors: Michael Schiappa, Chicago, IL (US); Kelsey Witt, Cardiff By the Sea, CA (US); Hunter Stahl, Boston, MA (US); Roberta Blaho, Columbus, OH (US)

(73) Assignee: OCA HOLDINGS LLC, Lincolnwood, IL (US)

( * ) Notice: Subject to any disclaimer, the term of this patent is extended or adjusted under 35 U.S.C. 154(b) by 990 days.

(21) Appl. No.: 16/907,389

(22) Filed: Jun. 22, 2020

(65) Prior Publication Data

US 2021/0008321 A1    Jan. 14, 2021

Related U.S. Application Data

(60) Provisional application No. 62/871,443, filed on Jul. 8, 2019.

(51) Int. Cl.
*A61M 16/08* (2006.01)
*A61M 16/00* (2006.01)
*A61M 16/04* (2006.01)

(52) U.S. Cl.
CPC ...... *A61M 16/085* (2014.02); *A61M 16/0003* (2014.02); *A61M 16/0493* (2014.02); *A61M 2205/75* (2013.01); *A61M 2210/0625* (2013.01); *A61M 2230/432* (2013.01)

(58) Field of Classification Search
None
See application file for complete search history.

(56) References Cited

U.S. PATENT DOCUMENTS

| | | |
|---|---|---|
| 2,908,269 A | 10/1959 | Cheng |
| 4,166,467 A | 9/1979 | Abramson |
| 4,527,559 A | 7/1985 | Roxburg et al. |
| 4,896,667 A | 1/1990 | Magnuson et al. |
| 5,655,519 A | 8/1997 | Alfery |
| 2007/0006878 A1* | 1/2007 | Mackey ............. A61M 16/085 128/200.26 |
| 2015/0190599 A1* | 7/2015 | Colman ................ A61B 5/097 600/531 |

* cited by examiner

*Primary Examiner* — Jay B Shah
(74) *Attorney, Agent, or Firm* — Klintworth & Rozenblat IP LLP

(57) ABSTRACT

An oral capnography accessory device provides a pathway for sampling oral exhalations of carbon dioxide from a mouth of a patient. The device is used in combination with a bite block. The device includes a main body extending linearly along a longitudinal axis, latch arms extending from a buccal facing surface of the main body and forming a cavity into which the bite block is insertable, and tube attachment extending from a lingual facing surface of the main body. Tubing is insertable through a passageway therethrough of the tube attachment. The device is configured for use with a nose or face mask, and with a monitoring system.

20 Claims, 5 Drawing Sheets

ORAL CAPNOGRAPHY ACCESSORY DEVICE

CROSS-REFERENCE TO RELATED APPLICATION(S)

This application claims priority to U.S. provisional application Ser. No. 62/871,443, filed on Jul. 8, 2019, the contents of which are incorporated herein in its entirety.

FIELD OF THE DISCLOSURE

The present disclosure relates to an oral capnography accessory device which provides a pathway for sampling oral exhalations of carbon dioxide ($CO_2$) from a mouth of a patient.

BACKGROUND

In any surgical procedure that requires deep or moderate sedation, end-tidal carbon dioxide ($EtCO_2$) is an invaluable vital sign due to its minimal lag time in reporting any changes in ventilation compared to the significantly longer delay inherent in peripheral capillary oxygen saturation ($SpO_2$) reading. Capnography provides monitoring of breathing disorders affecting an individual in real time during a surgery.

U.S. Pat. No. 2,908,269 describes an "Endotracheal Tube Holder and Bite Block". U.S. Pat. No. 5,655,519 describes a "Patient Airway Bite Block". U.S. Pat. No. 4,896,667 describes an "Endotracheal Tube Bite Block". U.S. Pat. No. 4,527,559 describes an "Endotracheal Tube Anchoring Mechanism". U.S. Pat. No. 4,166,467 describes a "Bite Block for Endotracheal Tube".

SUMMARY

An oral capnography accessory device in accordance with example embodiments provides a pathway for sampling oral exhalations of carbon dioxide from a mouth of a patient. The oral capnography accessory device is used in combination with a bite block. The oral capnography accessory device includes a main body extending linearly along a longitudinal axis, latch arms extending from a buccal facing surface of the main body and forming a cavity into which the bite block is insertable, and tube attachment extending from a lingual facing surface of the main body. Tubing is insertable through a passageway therethrough of the tube attachment.

An assembly including the oral capnography accessory device is provided. The assembly may include a nose or face mask, and a monitoring system.

BRIEF DESCRIPTION OF THE DRAWINGS

The organization and manner of the structure and operation of the disclosed embodiments, together with further objects and advantages thereof, may best be understood by reference to the following description, taken in connection with the accompanying drawings, which are not necessarily drawn to scale, wherein like reference numerals identify like elements in which.

DETAILED DESCRIPTION

Figure 1:
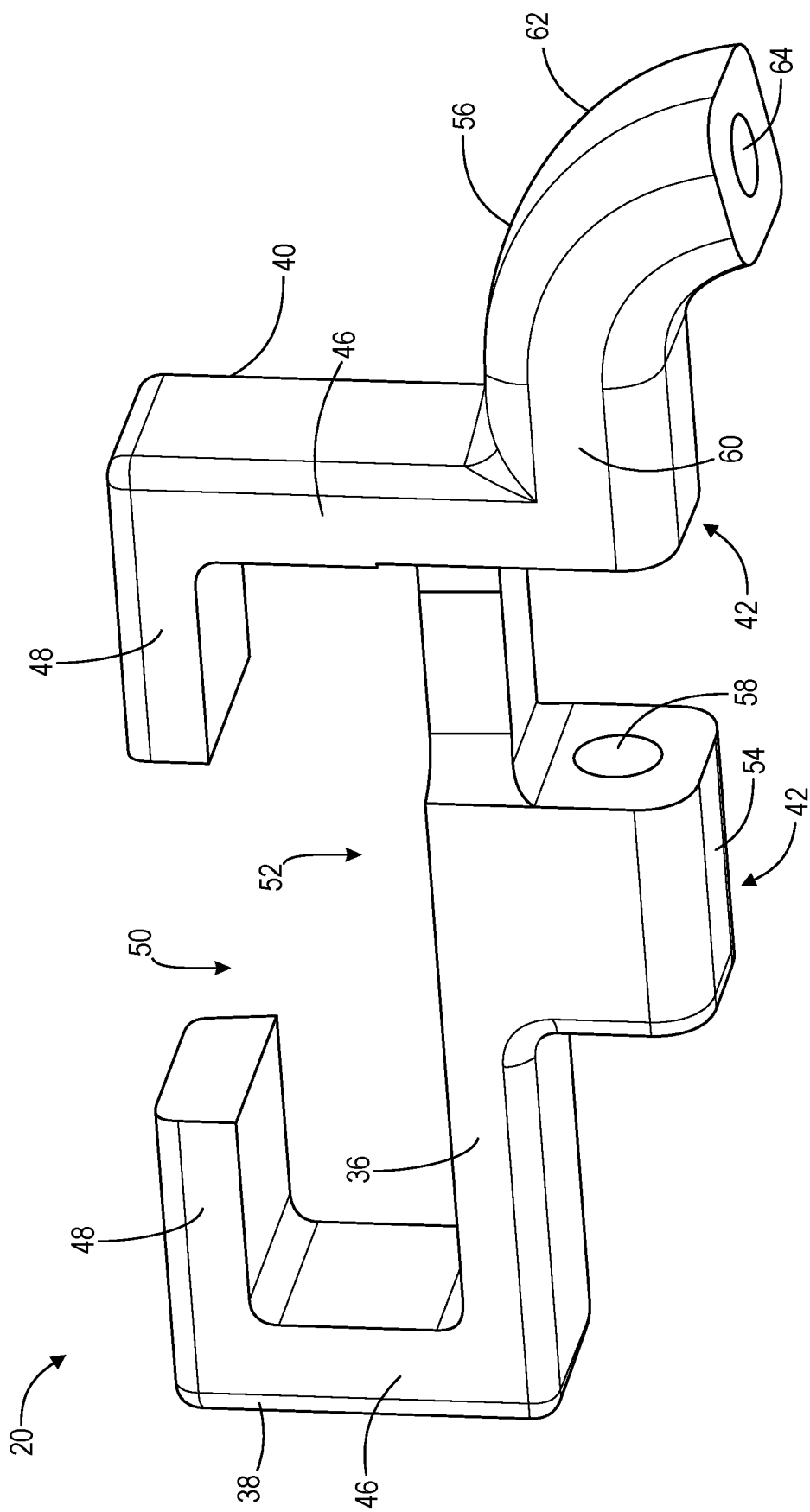
FIG. 1 depicts a perspective view of an oral capnography accessory device.

While the disclosure may be susceptible to embodiment in different forms, there is shown in the drawings, and herein will be described in detail, a specific embodiment with the understanding that the present disclosure is to be considered an exemplification of the principles of the disclosure, and is not intended to limit the disclosure to that as illustrated and described herein. Therefore, unless otherwise noted, features disclosed herein may be combined together to form additional combinations that were not otherwise shown for purposes of brevity. It will be further appreciated that in some embodiments, one or more elements illustrated by way of example in a drawing(s) may be eliminated and/or substituted with alternative elements within the scope of the disclosure.

A single-use oral capnography accessory device 20 is provided. The oral capnography accessory device 20 is used to provide a pathway for sampling oral exhalations of carbon dioxide ($CO_2$) from a mouth 22 of a patient 24 and is mounted on a conventional bite block 26, see FIG. 5, which is also commonly referred to as a mouth prop. The oral capnography accessory device 20 increases the accuracy of carbon dioxide ($CO_2$) sampling from the mouth 22 of a patient 24, thereby providing a more reliable capnography reading. The oral capnography accessory device 20 is minimally intrusive on surgery and can be incorporated into a prior art monitoring system.

Figure 5:
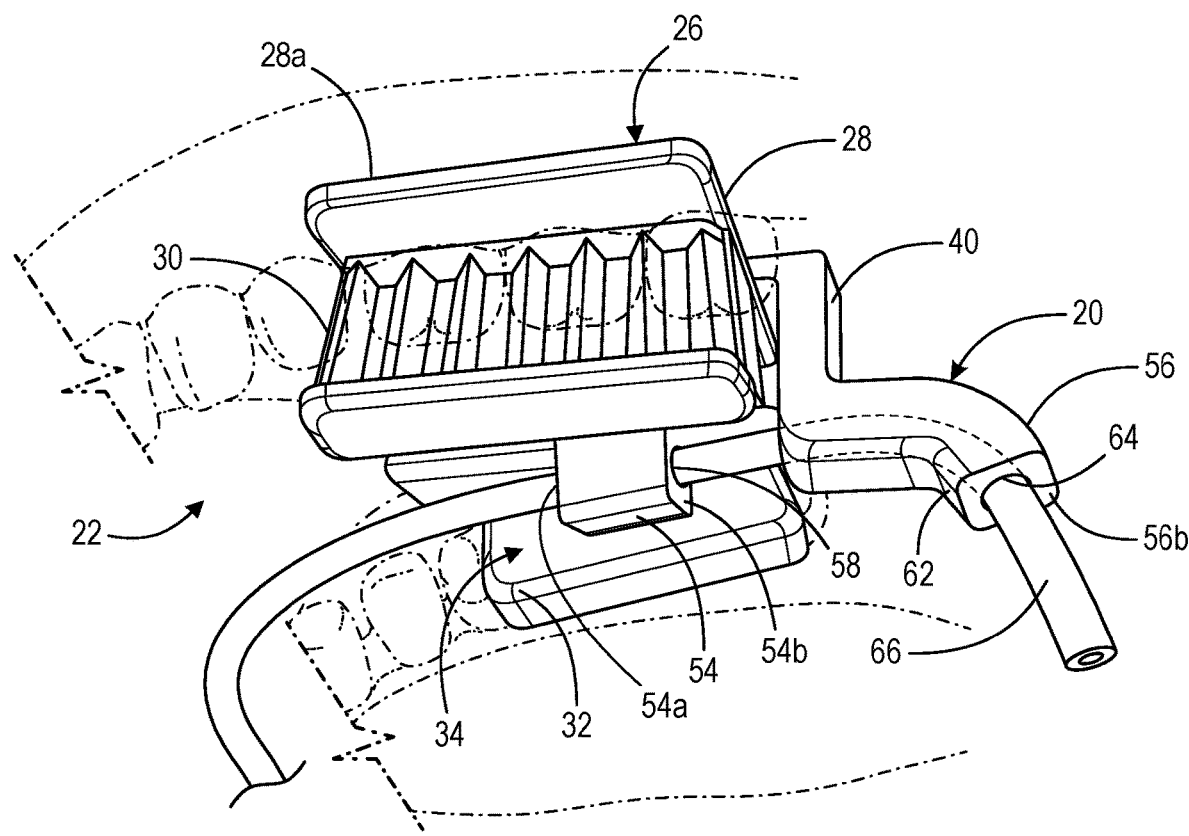
FIG. 5 depicts a perspective view of the oral capnography accessory device mounted on a bite block and shown held in the teeth of a patient; the teeth being shown in dotted line.

Bite blocks 26 are known in the art. An example bite block 26 is shown in FIG. 5. As shown, the bite block 26 has planar buccal plate 28 which when placed in the mouth 22 faces the cheek of the patient 24. The bite block 26 further has a pair of spaced apart teeth engaging flanges 30, 32, each extending perpendicularly outwardly from a lingual facing side 28_a_ of the buccal plate 28 from a first end of the buccal plate 28 to a second end of the buccal plate 28. A lingual channel 34 is provided by the buccal plate 28 and the flanges 30, 32. In use, the buccal plate 28 is proximate to the cheek of the patient 24 and the patient's upper teeth engage an outer surface of one of the flanges, for example flange 30 and the patient's lower teeth engage an outer surface of the other one of the flanges, for example flange 32. The lingual channel 34 faces the tongue of the patient 24.

Figure 2:
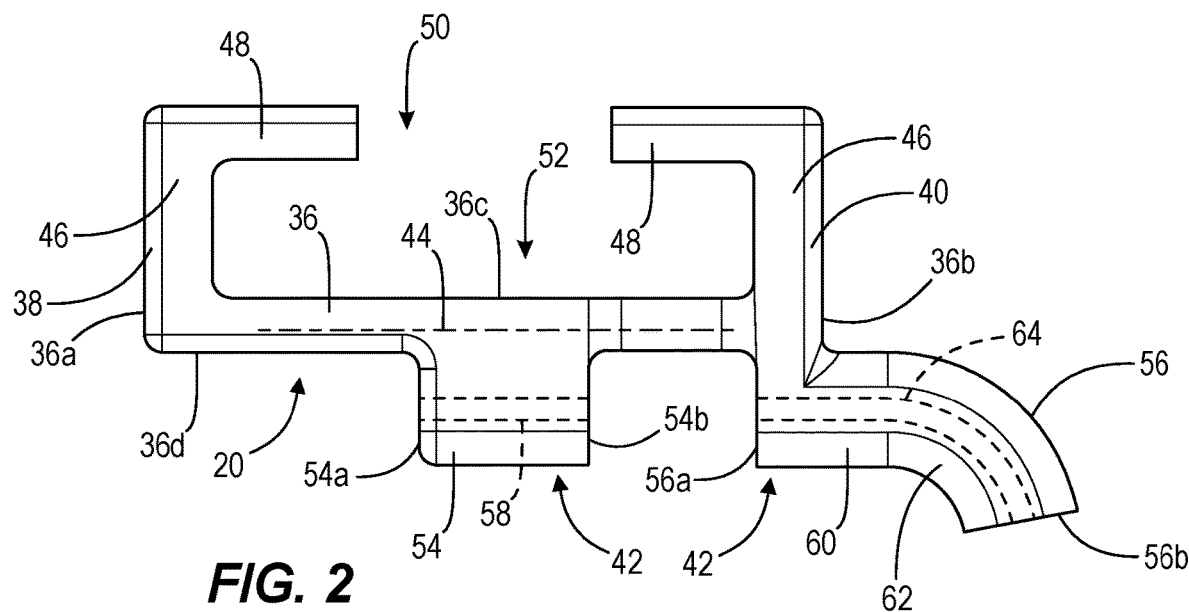
FIG. 2 depicts a top plan view of the oral capnography accessory device.
Figure 3:
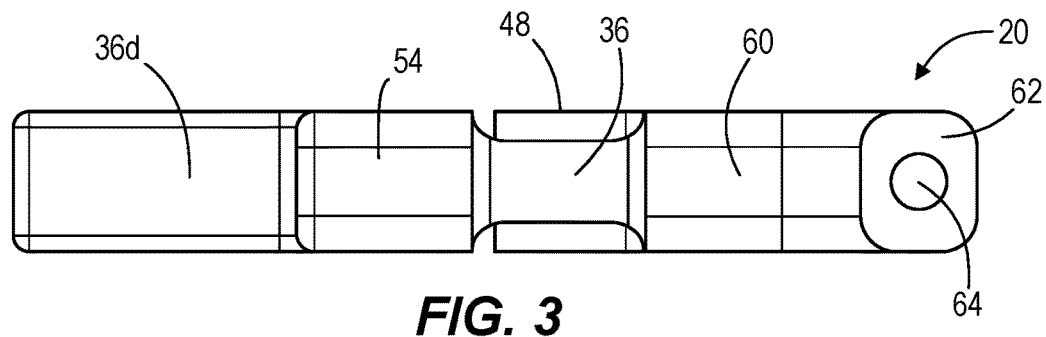
FIG. 3 depicts a bottom plan view of the oral capnography accessory device.
Figure 4:
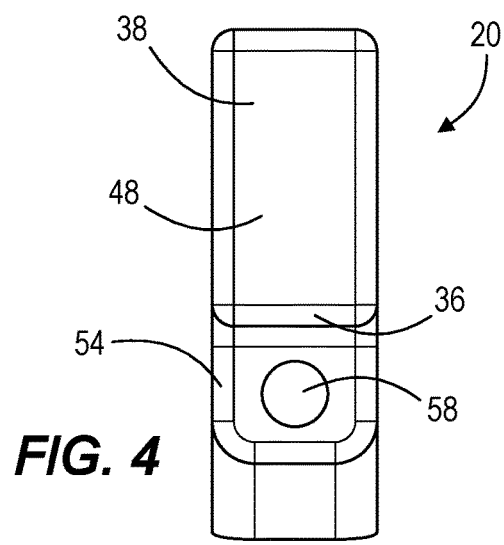
FIG. 4 depicts a front plan view of the oral capnography accessory device.

As best shown in FIGS. 1 and 2, the oral capnography accessory device 20 is formed from a main body 36, a first latch arm 38 extending from the main body 36, a second latch arm 40 extending from the main body 36, and a tube attachment 42 extending from the main body 36. The oral capnography accessory device 20 attaches directly to a conventional bite block 26, such as the one described herein.

The main body 36 has a first and second ends 36_a_, 36_b_ and extends longitudinally along a longitudinal axis 44 between the ends 36_a_, 36_b_. The main body 36 defines a buccal or cheek facing surface 36_c_ between the ends, and an opposite lingual or tongue facing surface 36_d_ between the ends 36a, 36b. In an embodiment, the main body 36 is a rectangular prism, but the main body 36 may take other forms, such as a cylinder.

The first latch arm 38 extends from the buccal facing surface 36c at the first end 36a of the main body 36, and the second latch arm 40 extends from the buccal facing surface 36c at the second end 36b of the main body 36. Each latch arm 38, 40 can be flexed outwardly from each other. When in an unflexed condition, each latch arm 38, 40 is generally L-shaped and has a first arm section 46 which extends perpendicular to the buccal facing surface 36c of the main body 36, and a second arm section 48 which extends perpendicular to the first arm section 46. Ends of the respective second arm sections 48 face each other, and are spaced apart from each other such that an opening 50 is formed therebetween. When in an unflexed condition, the main body 36 and the latch arms 38, 40 form a generally rectangularly shaped cavity 52 therein; the cavity 52 is in communication with the opening 50. When in a flexed condition, the opening 50 is increased in size versus the unflexed condition.

The tube attachment 42 extends from the lingual facing surface 36d of the main body 36. In an embodiment, the tube attachment 42 includes a first attachment portion 54 and a second attachment portion 56. The first attachment portion 54 extends outwardly from the main body 36, is spaced from the first and second ends 36a, 36b, and is parallel to, or generally parallel to, the longitudinal axis 44 of the main body 36. A passageway 58 extends through the first attachment portion 54 from a first end 54a thereof to a second end 54b thereof and is parallel to, or generally parallel to, the longitudinal axis 44 of the main body 36. The second attachment portion 56 generally takes the shape of a "dog leg" and has a first section 60 that extends outwardly from the second end 36b of the main body 36 and is parallel to, or generally parallel to, the longitudinal axis 44 of the main body 36, and further has a second section 62 which is curved relative to the longitudinal axis 44 of the main body 36 and extends outwardly from a second end of the first section 60. A first end 56a of the second attachment portion 56 is longitudinally spaced from the second end 54b of the first attachment portion 54. The second section 62 curves outwardly from the longitudinal axis 44 of the main body 36 such that the second end 56b of the second attachment portion 56 is offset from the longitudinal axis 44 of the main body 36. A passageway 64 extends through the second attachment portion 56 from the first end 56a thereof to a second end 56b thereof and has a first portion that is parallel to, or generally parallel to, the longitudinal axis 44 of the main body 36 and a second portion that curves relative to the longitudinal axis 44 of the main body 36. The passageways 58, 64 through the first attachment portion 54 and through the first section 60 of the second attachment portion 56 longitudinally align with each other. While two separate attachment portions 54, 56 are shown and described, it is to be understood that a single attachment portion with a single passageway may be provided.

As shown in FIG. 5, prior to attachment of the oral capnography accessory device 20 to the bite block 26 as described herein, or after attachment of the oral capnography accessory device 20 to the bite block 26 as described herein, conventional flexible, plastic, water resistant tubing 66 is inserted through the passageways 58, 64 (or single passageway) in the attachment portions 54, 56 (or single attachment portion) such that the tubing 66 extends outwardly from the first end 54a of the first attachment portion 54 and outwardly from the second end 56b of the second attachment portion 56.

To attach the oral capnography accessory device 20 to the bite block 26, the main body 36 is seated within the lingual channel 34 of the bite block 26 and the latch arms 38, 40 engage the first and second ends of the buccal plate 28 of the bite block 26 as shown in FIG. 5. If necessary, the latch arms 38, 40 can be flexed outwardly from each other to accommodate bite blocks 26 which have a longer buccal plate 28 than the distance between the latch arms 38, 40. The first attachment portion 54 seats within the lingual channel 34, and the second attachment portion 56 extends outwardly from the second end of the buccal plate 28 of the bite block 26.

In use, the bite block 26 and attached oral capnography accessory device 20 are inserted between the teeth of a patient 24 with the second section 62 of the second attachment portion 56 being closest to the throat of the patient 24. The tubing 66 extending from the first attachment portion 54 extends outwardly from the mouth 22 of the patient 24. The buccal plate 28 is positioned proximate to the cheek of the patient 24 and the patient's upper teeth engage the outer surface of one of the flanges, for example flange 30 and the patient's lower teeth engage an outer surface of the other one of the flanges, for example flange 32. The first attachment portion 54 faces the tongue of the patient 24. As a result, the oral capnography accessory device 20 is firmly affixed to the bite block 26 during oral surgery.

Use of the oral capnography accessory device 20 mounted on the bite block 26 allows for oral exhalations of the patient 24 to be effectively sampled during oral and maxillofacial surgery. Since the oral capnography accessory device 20 does not cover the mouth 22 of the patient 24, the surgeon is provided with the ability to access the mouth 22 of the patient 24. The oral capnography accessory device 20 provides reliable capnography readings, especially in the case of mouth breathing.

The oral capnography accessory device 20 enables the tubing 66 to be positioned within 10 mm of the top of the patient's airway, and at a minimum of 5 cm away from the back of the patient's throat. The oral capnography accessory device 20 is small and lightweight, for example, the oral capnography accessory device 20 may have a volume of less than 4 $cm^3$ and a weight of 100 g. The oral capnography accessory device 20 is robust and can withstand 10 lbs of force before fracturing and 2 lbs of force before dislodging from the bite block 26. The oral capnography accessory device 20 is made of a biocompatible and resilient material. The oral capnography accessory device 20 may be molded from polyurethane, with a Shore A hardness of 90 to accomplish these specifications.

Figure 6:
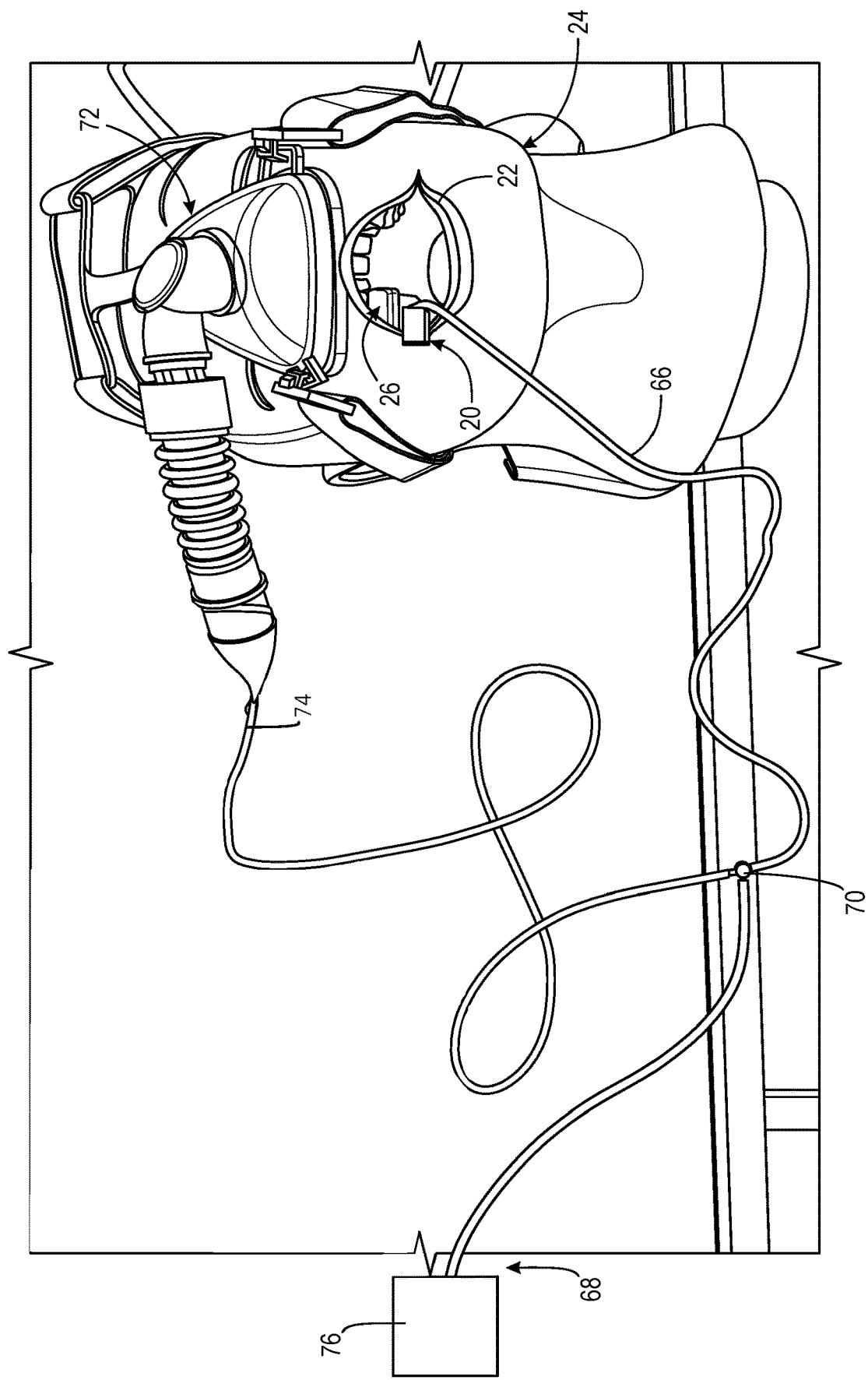
FIG. 6 depicts a perspective view of the oral capnography accessory device and the patient and showing a conventional monitoring system used therewith.

As shown in FIG. 6, the oral capnography accessory device 20 can be incorporated into a conventional monitoring system 68 commonly used in oral and maxillofacial surgery through the use of a three-way luer lock connector 70. In some embodiments, a nose or face mask 72 connected to tubing 74 is also provided in the system 68. Output from the tubing 66 of the oral capnography accessory device 20 (and outputs from the tubing 74 attached to the nose or face mask 72 if provided) and are analyzed at a mainstream or side stream capnography monitor 76. The capnography monitor 76 outputs capnography information to the physician. If the nose or face mask 72 is provided, the outputs from the tubing 66, 74 may be combined prior to input into the capnography monitor 76.

Figure 7:
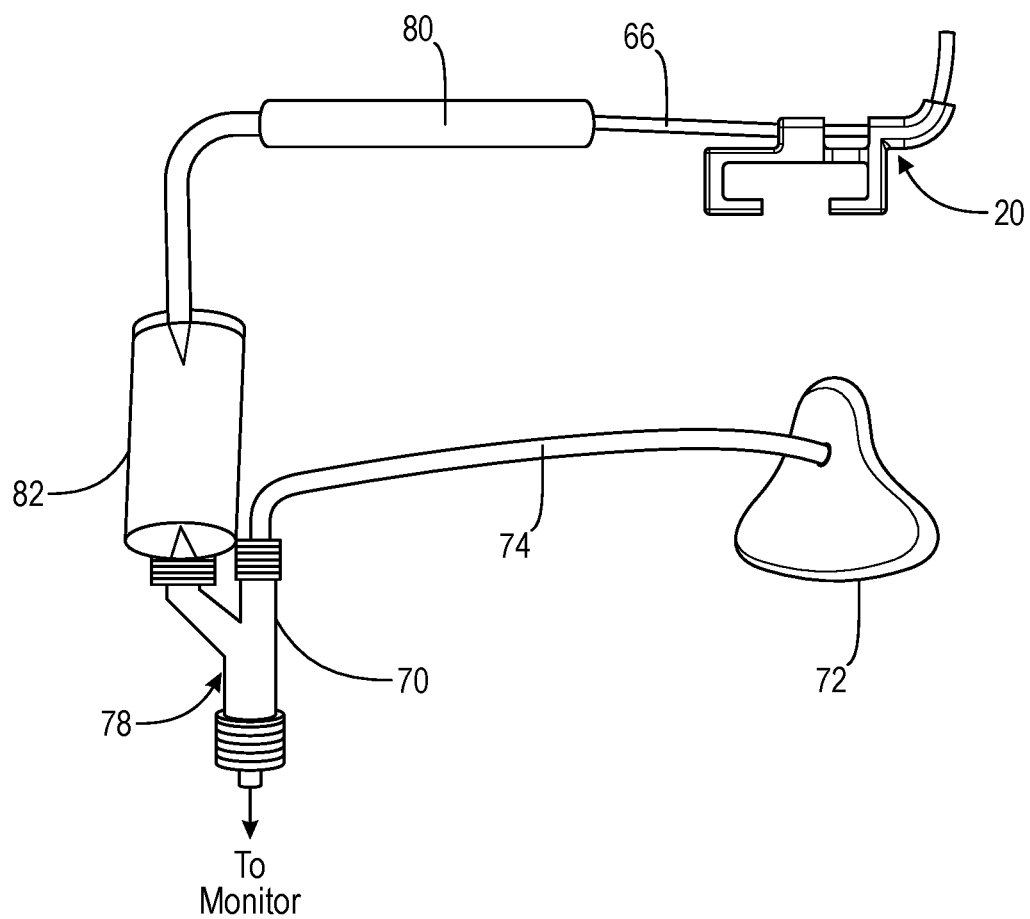
FIG. 7 depicts a perspective view of the oral capnography accessory device shown with nose or face mask.

The oral capnography accessory device 20 may be used with a fluid aspiration prevention unit 78 as shown in FIG. 7. The fluid aspiration prevention unit 78 minimizes the amount of water, blood, and debris that enters into the tubing 66 from the mouth 22 of the patient, and that ultimately enters the capnography monitor 76. The fluid aspiration prevention unit 78 includes a hydrophobic coating on the proximal end of the tubing 66 to prevent any visible fluid from entering into three-way luer lock connector 70. A water vapor permeable tubing segment 80 is located along the length of the tubing 66 between the oral capnography accessory device 20 and the capnography monitor 76 and allows for water vapor to be filtered out from the tubing 66. A male luer lock is provided at the end of the tubing 66 and connects to a female luer lock on a small fluid trap 82 downstream of the water vapor permeable tubing segment 80 to collect any remaining fluid in the tubing 66. The fluid trap 82 is upstream of and connected to the three-way luer lock connector 70. The three-way luer lock connector 70 has a female luer lock to connect to the tubing 74, and a male luer lock which connects to the capnography monitor 76.

To further improve carbon dioxide ($CO_2$) sampling, the oral capnography accessory device 20 may be used in combination with a conventional nose or face mask 72 which samples carbon dioxide ($CO_2$) sampling from the nose of a patient 24. Nose or face masks 72 are known in the art. An example nose mask 72 is shown in FIGS. 5 and 6 and has a dome-like canopy which has a flexible cushion surrounding the lower end of the canopy. Straps attach the canopy to the patient's face and the nose of the patient 24 seats within the cavity formed by the canopy. The tubing 74 is attached to the canopy and in communication with the cavity. The oral capnography accessory device 20 provides accuracy of carbon dioxide ($CO_2$) sampling from the mouth 22 of a patient 24, and when used with the nose mask, increased accuracy of carbon dioxide ($CO_2$) sampling is achieved from the mouth 22 and the nose of a patient 24.

Many modifications and other embodiments of the disclosure set forth herein will come to mind to one skilled in the art to which these disclosed embodiments pertain having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the disclosure. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the disclosure. In this regard, for example, different combinations of elements and/or functions than those explicitly described above are also contemplated within the scope of the disclosure. Although specific terms are employed herein, they are used in a generic and descriptive sense only and not for purposes of limitation.

While particular embodiments are illustrated in and described with respect to the drawings, it is envisioned that those skilled in the art may devise various modifications without departing from the spirit and scope of the appended claims. It will therefore be appreciated that the scope of the disclosure and the appended claims is not limited to the specific embodiments illustrated in and discussed with respect to the drawings and that modifications and other embodiments are intended to be included within the scope of the disclosure and appended drawings. Moreover, although the foregoing descriptions and the associated drawings describe example embodiments of elements and/or functions, it should be appreciated that different combinations of elements and/or functions may be provided by alternative embodiments without departing from the scope of the disclosure and the appended claims.

What is claimed is:

1. An oral capnography accessory device for use with a bite block, the oral capnography accessory device comprising:
   a main body extending linearly along a longitudinal axis, the main body having first and second opposite ends, a buccal facing surface extending between the ends and an opposite lingual facing surface extending between the ends;
   a first latch arm extending from the buccal facing surface at the first end of the main body;
   a second latch arm extending from the buccal facing surface at the second end of the main body, wherein an opening is provided between the latch arms, and wherein the latch arms and main body form a cavity into which the bite block is insertable, the cavity being in communication with the opening; and
   a tube attachment extending from the lingual facing surface of the main body, the tube attachment having a passageway therethrough.

2. The oral capnography accessory device of claim 1, wherein the passageway has a first portion which extends parallel to the longitudinal axis of the main body and has a second portion which is curved relative to the longitudinal axis of the main body.

3. The oral capnography accessory device of claim 2, further comprising tubing extending through the passageway.

4. The oral capnography accessory device of claim 1, further comprising tubing extending through the passageway.

5. The oral capnography accessory device of claim 1, wherein each latch arm comprises a first portion which extends perpendicular to the main body and a second portion which is perpendicular to the first portion, wherein the opening is between the second portions.

6. The oral capnography accessory device of claim 5, wherein the latch arms are flexible such that the opening can be increased in size.

7. The oral capnography accessory device of claim 1, wherein the oral capnography accessory device is formed of polyurethane.

8. An oral capnography accessory device for use with a bite block, the oral capnography accessory device comprising:
   a main body extending linearly along a longitudinal axis, the main body having first and second opposite ends, a buccal facing surface extending between the ends and an opposite lingual facing surface extending between the ends;
   a first flexible latch arm extending from the buccal facing surface at the first end of the main body;
   a second flexible latch arm extending from the buccal facing surface at the second end of the main body, each latch arm including a first portion which extends perpendicular to the main body and a second portion which is perpendicular to the first portion, wherein an opening is provided between the second portions of the latch arms, and wherein the latch arms and main body form a cavity into which the bite block is insertable, the cavity being in communication with the opening; and a tube attachment extending from the lingual facing surface of the main body, the tube attachment having a passageway therethrough, the passageway having a first portion which extends parallel to the longitudinal axis of the main body and having a second portion which is curved relative to the longitudinal axis of the main body.

9. The oral capnography accessory device of claim 8, further comprising tubing extending through the passageway.

10. The oral capnography accessory device of claim 8, wherein the oral capnography accessory device is formed of polyurethane.

11. An assembly for sampling oral exhalations of carbon dioxide from a mouth of a patient comprising:
an oral capnography accessory device, the oral capnography accessory device including
a main body extending linearly along a longitudinal axis, the main body having first and second opposite ends, a buccal facing surface extending between the ends and an opposite lingual facing surface extending between the ends,
a first latch arm extending from the buccal facing surface at the first end of the main body,
a second latch arm extending from the buccal facing surface at the second end of the main body, wherein an opening is provided between the latch arms, and wherein the latch arms and main body form a cavity in communication with the opening, and
a tube attachment extending from the lingual facing surface of the main body, the tube attachment having a passageway therethrough;
tubing extending through the passageway; and
a bite block mounted within the cavity.

12. The assembly of claim 11, further comprising:
capnography monitor connected to the tubing.

13. The assembly of claim 11, further comprising a fluid aspiration prevention unit including a hydrophobic coating on an end of the tubing.

14. The assembly of claim 11, wherein the tubing includes a water vapor permeable tubing segment configured to filter water vapor.

15. The assembly of claim 11, wherein the tubing extending from the oral capnography accessory device includes a water vapor permeable tubing segment configured to filter water vapor.

16. The assembly of claim 15, wherein the tubing extending from the oral capnography accessory device further includes a fluid trap downstream of the water vapor permeable tubing segment.

17. The assembly of claim 11, further comprising:
a nose or face mask;
tubing connected to the nose or face mask;
a connector connected to the tubing connected to the nose or face mask and connected to the tubing connected to the oral capnography accessory device; and
a capnography monitor connected to the connector.

18. The assembly of claim 17, further comprising a fluid aspiration prevention unit including a hydrophobic coating on an end of the tubing extending from the oral capnography accessory device.

19. The assembly of claim 18, wherein the tubing extending from the oral capnography accessory device includes a water vapor permeable tubing segment configured to filter water vapor.

20. The assembly of claim 19, wherein the tubing extending from the oral capnography accessory device further includes a fluid trap downstream of the water vapor permeable tubing segment and upstream of the fluid aspiration prevention unit.

* * * * *